United States Patent [19]

Torti et al.

[11] Patent Number: 5,057,281

[45] Date of Patent: Oct. 15, 1991

[54] ADJUSTABLE MULTI-CHANNEL PIPETTER

[75] Inventors: Victor A. Torti, Brookline; Gary E. Nelson, Hollis, both of N.H.; R. Laurence Keene, Brookline; George P. Kalmakis, Reading, both of Mass.

[73] Assignee: Matrix Technologies Corporation, Lowell, Mass.

[21] Appl. No.: 519,836

[22] Filed: May 7, 1990

[51] Int. Cl.$^5$ .............................................. B01L 3/02
[52] U.S. Cl. ................................... 422/100; 422/65; 422/104; 436/180; 73/863.32; 73/864.14
[58] Field of Search .............. 422/100, 99, 65, 104; 436/180; 73/863.32, 864.14, 864.16, 864.17

[56] References Cited

U.S. PATENT DOCUMENTS

| 4,599,220 | 7/1986 | Yonkers et al. | 73/864.17 X |
| 4,779,467 | 10/1988 | Rainin et al. | 422/100 X |
| 4,824,642 | 4/1989 | Lyman et al. | 422/100 |
| 4,830,832 | 5/1989 | Arpagaus et al. | 422/65 |

Primary Examiner—Robert J. Warden
Assistant Examiner—Lynn M. Kummert
Attorney, Agent, or Firm—Wolf, Greenfield & Sacks

[57] ABSTRACT

A pipetting system having a plurality of fittings whose spacing can be individually adjusted by sliding the fittings along a track. Changing the spacing is accomplished by releasing a clamping plate which secures the fittings to the track. The fittings are then slid into the desired position and reclamped. In addition, there is a stripper mechanism for removing disposable tips attached to the fittings. The release mechanism can be operated in any positioning of the fittings. The mechanism is trigger actuated.

20 Claims, 6 Drawing Sheets

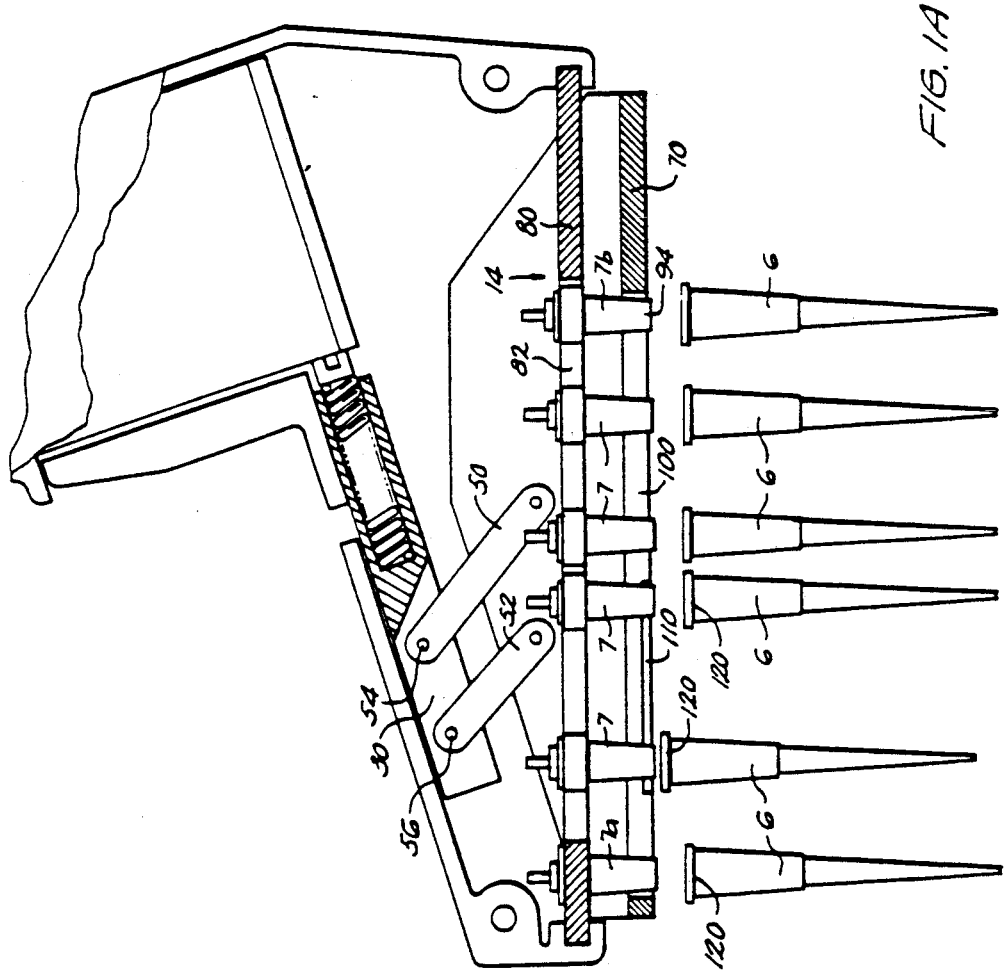

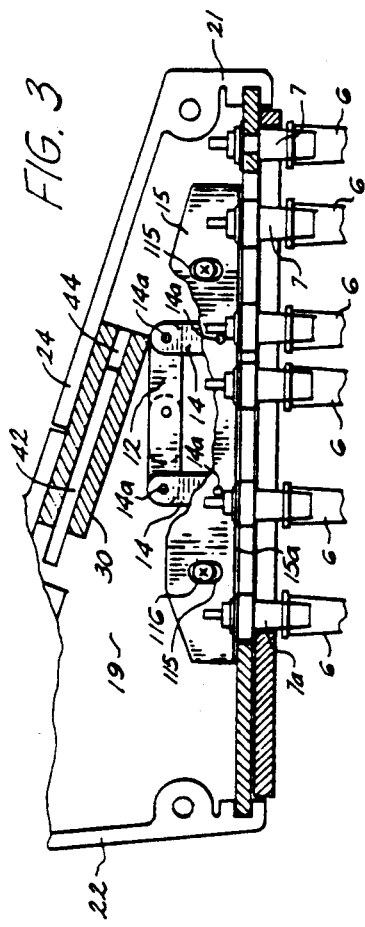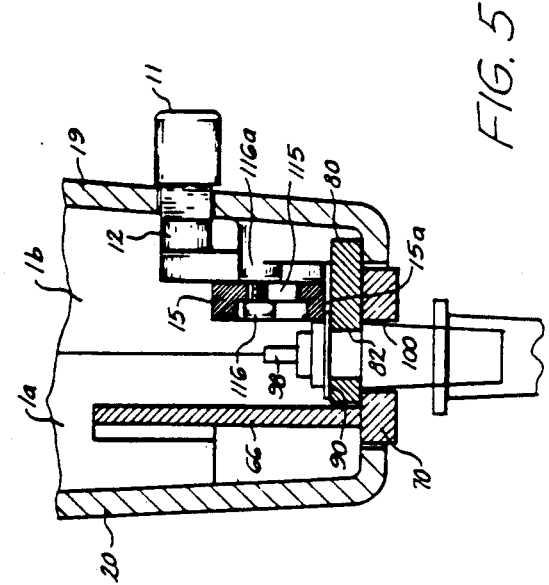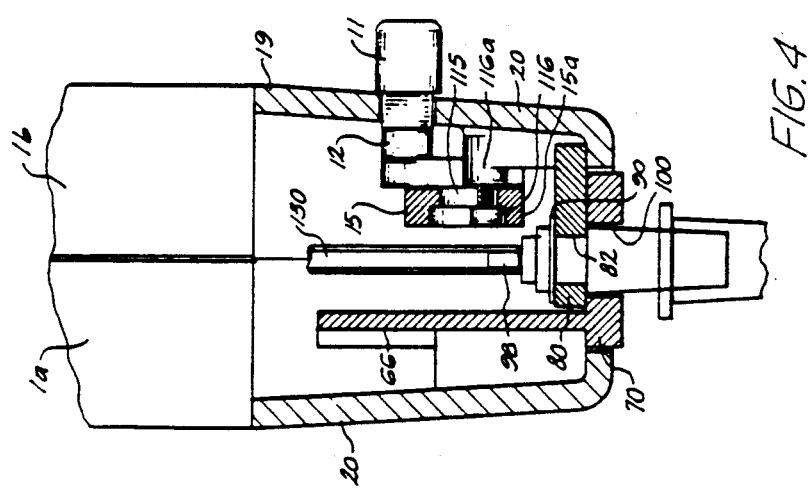

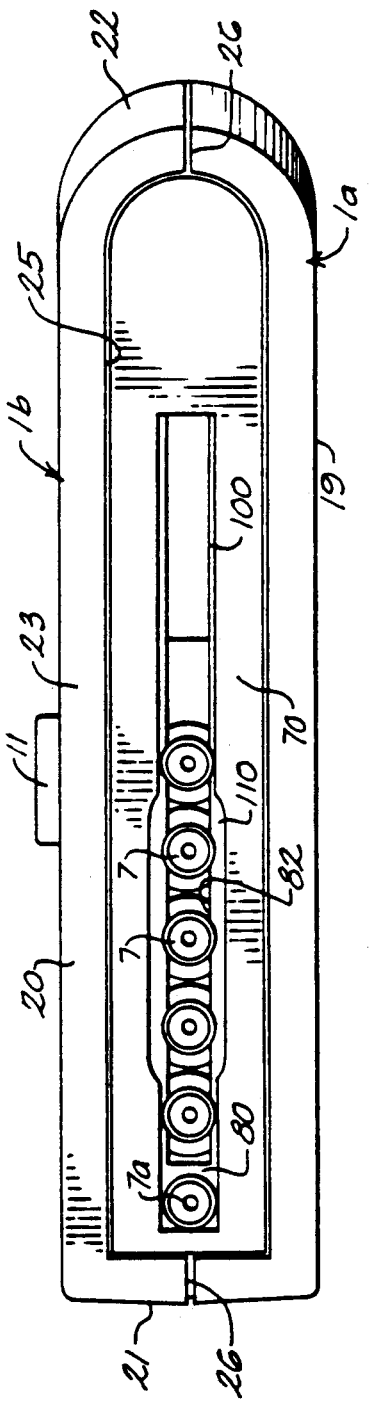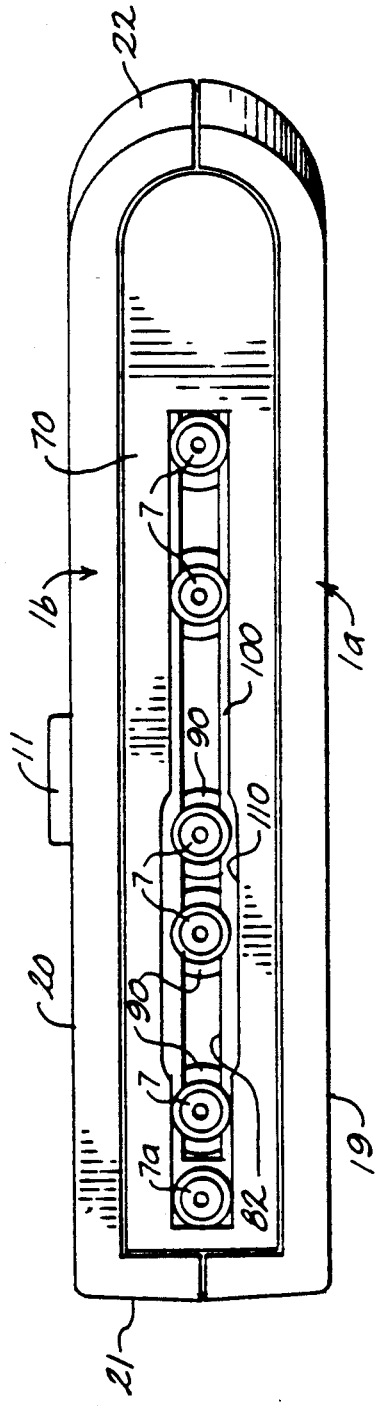

ADJUSTABLE MULTI-CHANNEL PIPETTER

BACKGROUND OF INVENTION

This invention relates to liquid transfer devices used in laboratories, and more particularly, is directed toward a multi-channel pipetting device which enables the user to adjust the spacings between individual pipette tips.

Pipetting systems are used in laboratories for the transfer of relatively small quantities of liquids. The liquid is normally drawn into the tips by suction and is subsequently released into the wells of microtiter plates or other receptacles. Frequently the transfer involves patient samples which are moved to receptacles which are unevenly spaced apart. Because virtually all hand operated multi-channel pipettes have a fixed spacing between pipette tips, the transfer must be made by single channel pipettes, which is a slow and very inefficient process. Some large laboratories and pharmaceutical firms which perform thousands of transfers a day have purchased fully automatic robotic systems that cost tens or hundreds of thousands of dollars, but those systems are beyond the reach of small and medium size firms.

One important object of this invention is to provide a pipetting system which is relatively inexpensive but which is capable of being adjusted to vary the spacing between the pipette tips so that liquid may be transferred to receptacles to another set of different spacing.

A more specific object of the present invention is to provide a pipetting system that enables the user to individually adjust the pipette tips from one set of spacings to another.

It is a further object of the present invention to provide a pipetting system that easily and effectively secures the pipette tips in the selected position.

It is a further object of the present invention to provide a pipetting system that is of simple construction and therefore relatively inexpensive to manufacture.

It is a further object of this invention to provide an adjustable pipetting system that is easy to operate and does not require complicated adjustments for use.

It is a further object of the present invention to provide a hand-held pipetter having a tip removing assembly that removes tips safely and efficiently without regard to the particular orientation of the tips.

It is a further object of the present invention to provide a pipetting system having a tip removing assembly that requires a minimum force to remove the tips.

The system is embodied in a boot-shaped instrument having a housing with a handle section and a foot or lower section. A plurality of fittings aligned in a row extend downwardly from the foot. The fittings are separate from one another and are slidably mounted on a track alone the foot such that the various positions ar limited by the length of the track and the width of the mountings that carry the fittings. A clamping plate inside the housing releasably secures the fittings to the track in any selected position.

A tip removing mechanism operated by a trigger on the handle section has a stripper that can remove the disposable tips from the fittings regardless of the spacing of the fittings. As the trigger is squeezed, the stripper pushes the tips off the fittings. In order to reduce the overall force required to eject the tips, the ejecting surface of the stripper is stepped so that groups of tips are engaged in sequence causing first one group and then another to be pushed off the fittings.

The many objects and features of this invention will be better understood and appreciated from the following detailed description of the preferred embodiment thereof read in connection with the accompanying drawings.

BRIEF FIGURE DESCRIPTION

FIG. 1A is a view similar to FIG. 1 but showing the stripper assembly in the actuating position to remove the tips from their holders;

FIG. 3 is a fragmentary cross-sectional view similar to FIG. but showing the clamping assembly in a locked position;

Figure 2:
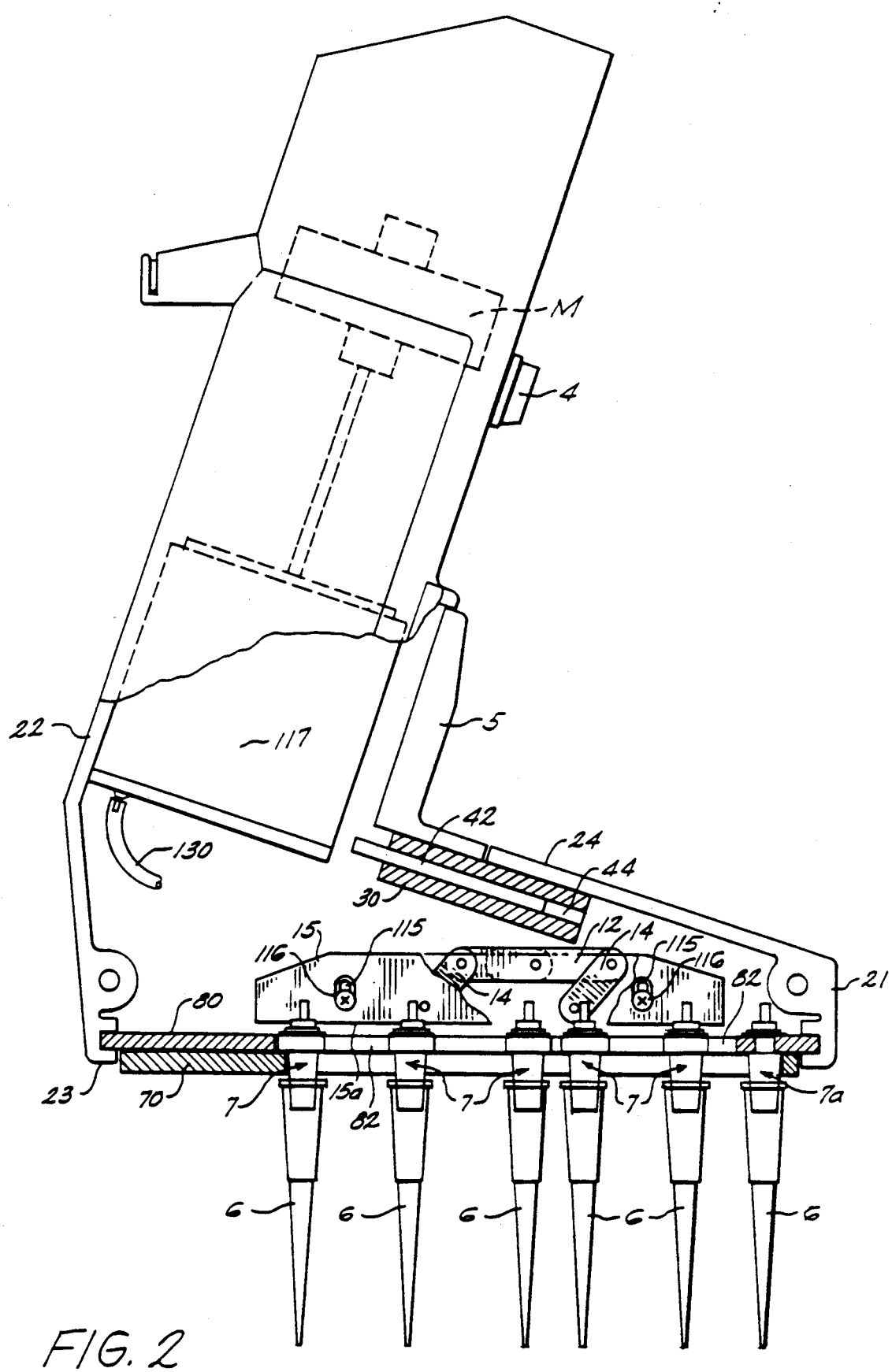
FIG. 2 is right side view, partially in cross-section of the pipetter of FIG. 1 and showing the details of the clamping assembly and with the clamping assembly in the released position.
Figure 6:
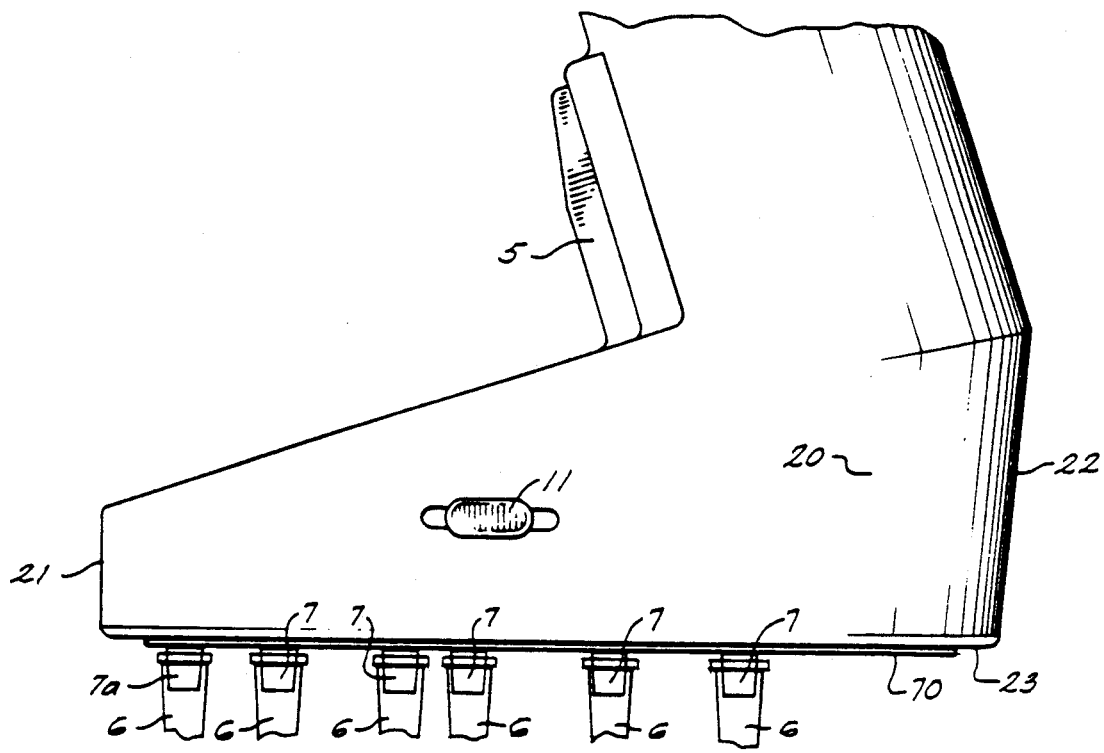
Figure 7:
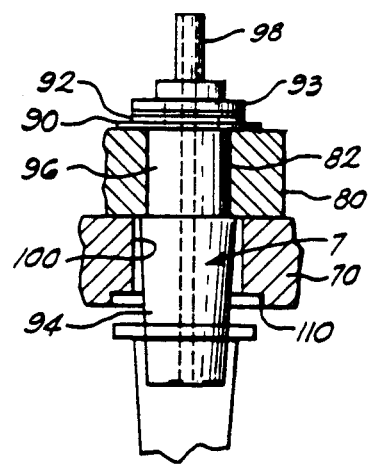

FIG. 4 and 5 are cross-sectional views taken along the section lines 4—4 and 5—5 in FIGS. 2 and 3 respectively;

FIG. 6 is a fragmentary side view of the foot of the pipetter;

FIG. 7 is a fragmentary cross sectional view showing the details of one of the tip fittings forming part of the pipetter of the invention; and FIG. 8 and 9 are bottom view of the pipetter showing the tip fittings in different position in the slot 82 of mounting plate 80.

DETAILED DESCRIPTION OF THE PREFERRED EMBODIMENT

Referring now to the drawings, the pipetter of the present invention has a boot shaped housing 1 consisting of a handle section 2 and a lower or foot section 3. The handle section 2 carries both a push button 4 for initiating the pipetting action and a trigger 5 forming part of a stripping mechanism for removing disposable tips 6 which are frictionally secured to tip fittings 7 that project from the bottom 8 of the lower housing section 3. A clamping assembly for holding the tip fittings in their selected position includes an actuating knob 11 which projects from one side of the lower section 3 and is attached within the housing 1 to a clamping bar 12 with which it moves. The details of the clamping assembly and the stripper mechanism are described more fully below.

The housing 1 of the pipetting system is made up of a pair of mating half shells 1a and 1b (see FIGS. 4 and 5) which include sidewalls 19 and 20, front and back walls 21 and 22 and bottom wall 23 that together define the handle section 2 and the lower section 3. The front, back and bottom of the lower section 3 are enclosed by the walls 19, 20, 21, 22 and 23 respectively, while the top of the bottom section forward of the handle is closed by wall 24. An elongated aperture 25 is provided in the bottom wall 23 and extends substantially the full length thereof symmetrical with respect to the parting line 2 that joins the two shells.

The push button 4 which extends forwardly from the front edge of the handle section 2 is normally at the height of one's second finger when the handle is engaged while the trigger 5 which also extends forwardly from the front wall of the handle is a the height of the 4th and 5th fingers. The trigger 5 is generally L-shaped having an upwardly extending section 28 along the front of the handle section 2 and base 29 which slides along the top wall 24 of the bottom section 3. The actuating knob 11 for the clamping mechanism projects from sidewall 19.

Figure 1:
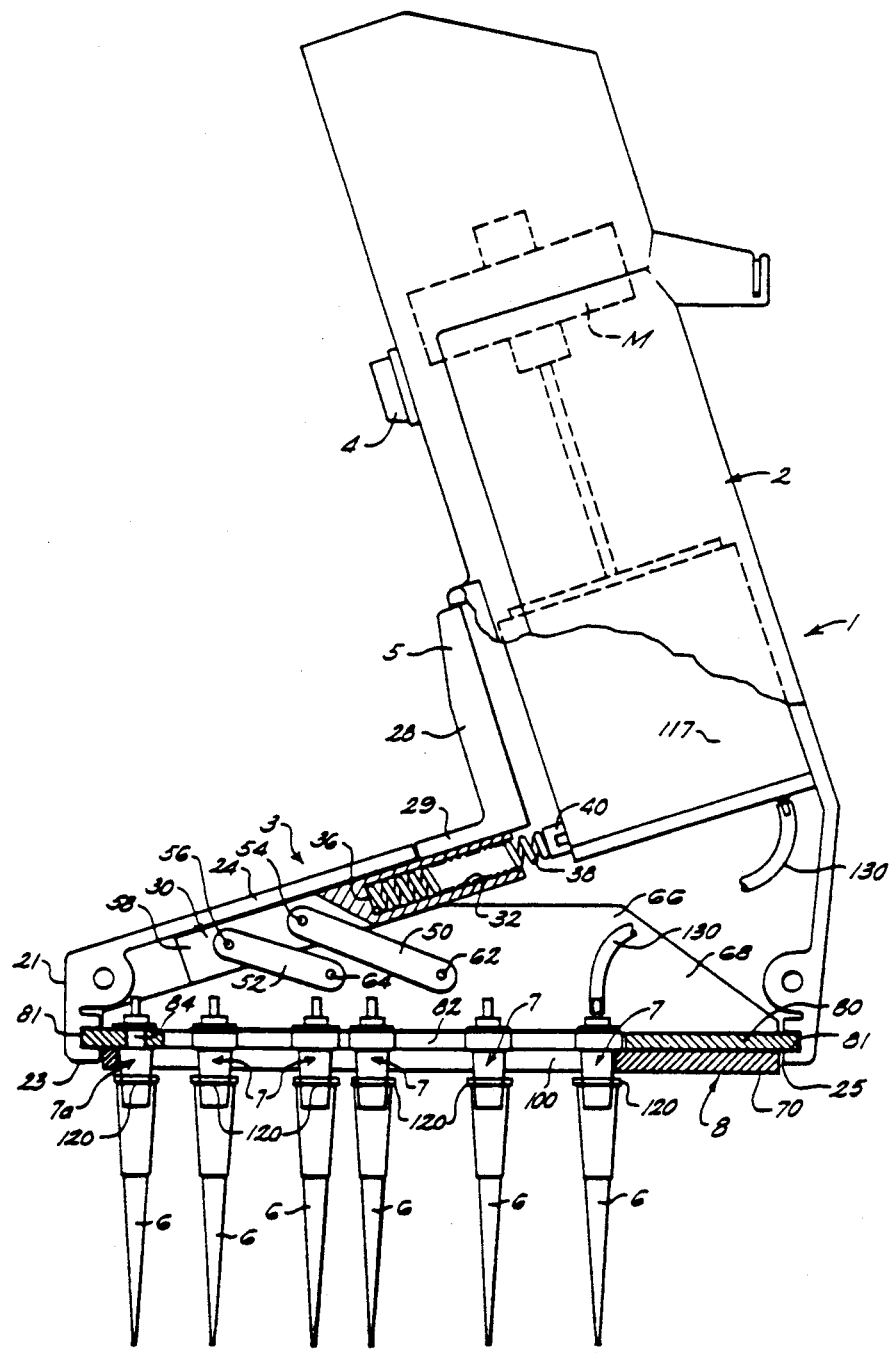
FIG. 1 is a left side view, partially in cross-section of a multi-channel pipetter constructed in accordance with this invention and showing the details of the stripper assembly.

The details of the pipetting system for drawing liquid in metered volumes into the tips 6 and for expelling the liquid from the tips is not part of the present invention and therefore is described only briefly herein. The system includes a cylinder 117 in the handle section 2 housing a plurality of parallel cylindrical chambers (not shown) that correspond in number to the number of fittings 7. In the embodiment shown, six fittings are included, but it should be appreciated that the number may vary. A piston (not shown) is slidably mounted in each chamber, and the pistons in turn are moved in tandem by a suitable electric motor M disposed in the handle section 2 above the cylinder 117. Each chamber is connected to one fitting 7 by a separate duct 130, only one of which is shown in FIGS. 1 and 2. Movement of the pistons by the motor M in on direction in their respective chambers draws liquid into the tips 6, and movement in the other direction expels the liquid from them. The motor in turn may be automatically controlled so as to program the volume of liquid drawn into and expelled from the tips during each actuation of the button 4 in the motor circuit. The button 4 is connected in the motor circuit to afford the operator control of the pipetting operation.

The trigger 5 may be integrally molded with a slide 30 that is disposed in the bottom section 3 of the housing immediately beneath top wall 24. The slide 30 has a recess 32 open to the rear and closed at its front end as shown at 36. A coil spring 38 is disposed in the recess 32 and bears against the end wall 36 at its front and against a barrier 40 carried in the rear of the half shell 1a of the housing. The slide 30 is carried by a pair of flanges 42 (one shown in FIGS. 2 and 3) provided on each half shell of the housing and which are disposed in slots 44 in the side edges of the slide. The spring 38 urges the slide in a forward direction toward the front wall or toe 21 of the lower section of the housing, but the spring may be overridden by squeezing the trigger 5, which will compress the spring and draw the slide in the direction of rear wall 22 to the position of FIG. 1A. When the trigger is released, the slide returns to the position shown in FIG. 1.

A pair of parallel links 50 and 52 are pivotally secured to the forward end of the slide 30 by a pair of pivot pins 54 and 56 that extend through holes in the upper ends of the links and which span the slot 58 formed in the slide 30 into which the links extend. The other ends of the links 50 and 52 are connected by means of pivot pins 62 and 64 to the vertical flange 66 of stripper plate 68. As will become apparent below, the stripper plate 68 is confined to vertical translational motion in housing 1, and that motion is imparted to the stripper plate by actuation of slide 30. As the slide 30 is actuated by trigger 5 against the bias of spring 38, the links 50 and 52 acting on the flange 66 urge the stripper plate 68 downwardly to the position shown in FIG.1A so that its horizontal flange 70 which performs the stripping action will force the tips 6 off the fittings 7. When the trigger 5 is released and the spring 38 forces the slide 30 to move in a forwardly direction, the links 50 and 52 draw the stripper plate upwardly in the housing to the retracted position of FIG. 1.

A tip fitting mounting plate 80 is secured immediately above the bottom of the housing by slots 81 formed in each half shell 1a and 1b (see FIGS. 1, 1A and 3). The mounting plate 80 includes an elongated slot 82 narrower and somewhat shorter than the opening 25 in the bottom wall 23. All but one (fitting 7a) of the fittings 7 is slidably mounted in the slot so that they may be moved toward and away from the front wall 21. The forward most fitting 7a is disposed in a separate opening 84 in the plate 80 and is immovable. The slot 82 forms a track for the fittings so as to guide their sliding motion to and fro along the bottom wall 23. Each of the fittings 7 disposed in the slot 82 has a truncated cone-shaped stem 94 having a diameter at its upper end which is larger than the width of slot 82, and consequently, the edges of the upper end of the stem bear against the lower surface of the mounting plate 80. Above the stem each fitting (excepting 7a) has a waist 96 which extends through the slot 82. A thin retaining plate 90 surrounds the upper end of the fitting, and the assembly is held together on the mounting plate 80 by a C-shaped clip 93. The upper end of each fitting carries a nipple 98 which in turn is connected to the lower end of one duct 130. It will, of course, be appreciated that a passage extends through each fitting from the lower end of the stem 94 to the upper end of nipple 98, which passage is in communication with the duct passage.

The fitting 7a is mounted in its opening 84 in the mounting plate 80 in precisely the same manner described above in connection with the other fittings 7 disposed in the slot 82. The only difference between the mounting of the other fittings and that of fitting 7a is that fitting 7a is rigidly secured in place and cannot move.

As described above, the horizontal flange 70 of the stripper plate 68 has a slot 100 formed therein through which the stems 94 of the fittings extend. The slot 100 in the flange does not interfere in any way with the sliding motion of the fittings in the the slot 82 of mounting plate 80. The slot 100 is, however, narrower than the outer diameter of the upper ends 120 of the tips 6 which are mounted on the stems 94 (see FIGS. 4, 5 and 7). Consequently, when the stripper plate is actuated by squeezing the trigger 5, the horizontal flange 70 moves downwardly toward the lower ends of the stems 94, and the sides of the slot 100 engage the upper ends 120 of the tips to push them off the fittings 7.

It will be noted in FIGS. 1A, 8 and 9 that steps 110 are provided in the sides of the slot 100 in flange 70. As a result, when the trigger 5 is squeezed, those tips 6 which are in the path of the steps 110 in the margin are engaged by the flange after the other tips are engaged by the flange. Consequently, the stripper plate 68 does not simultaneously engage all of the tips but rather their engagement is staggered so that a reduced force is required to eject them. First the tips aligned with the portions of the slot 100 which do not include the stepped edge 100 are ejected, and thereafter those aligned with the stepped edges are ejected as suggested in FIG. 1A.

It will be noted that when the fittings 7 are in the spaced relationship of FIG. 1A, two of the fittings are aligned with the steps 110 and four are not. Consequently when the trigger 5 is squeezed initially, three tips will be ejected, and then the remaining tips will be ejected. While it is possible that none of the fittings will be aligned with the steps 110, it should also be noted that more than one pair of steps may be used and the steps can be of any selected length.

It will be appreciated that in the manufacture of the pipetter shown, the maximum spacing of the tips and fittings 6 and 7 is dependent upon the length of the mounting plate 80 and its slot 82. Obviously in assembling the device, different plates having slots 82 of different lengths may be used as well. It is essential, however, that the fittings be maintained in parallel relationship so that the tips 6 mounted o them will remain parallel with one another. This is, of course, true whether the pipetter has six or a different number of channels.

The clamping assembly for the fitting as shown in FIGS. 2-6 includes a clamping plate 15 having vertical slots 115 that slidably receive screws 116 mounted in bosses 116a on the inside of wall 19. The movement of the clamping plate is confined to a vertical direction by the screws and slots. The clamping plate 15 is connected by a pair of links 14 to the clamping bar 12. The links 14 are connected to clamping bar 12 and plate 15 by pivot rivets 14a. Consequently, when the actuating knob 11 is moved to the left as viewed in FIG. 2 and carries bar 12 with it, the links 14 force the clamping plate 15 downwardly on the screws 116, and the lower edge 15a of the plate 15 bears against the retaining plates 90 to tightly secure the fittings against the mounting plate 80 as shown in FIGS. 3 and 5. Because the bar 12 is limited to a horizontal translational motion and the plate 15 is limited to a vertical motion, when the fittings are locked in place, movement of the knob 11 to the right will raise the plate and release the fittings as shown in FIG. 2 and 4 so that their positions may be manually adjusted by the user. Thus, the user can select any spacing desired for the individual fittings 6 and the space between adjacent fittings need not be uniform. By merely unlocking the clamping assembly by moving the knob 11, the user can make the position adjustments required, and the user can secure the fittings in place by relocking the clamping assembly. For example, in FIG. 1 and 8, the fittings 7 are shown in non uniformly spaced and in FIG. 9 a different spacing arrangement is shown.

Having described this invention in detail, those skilled in the ar will appreciate that numerous modifications may be made thereof without departing from its spirit. Therefore, it is not intended to limit the breadth of this invention to the single embodiment illustrated and described. Rather, it is intended that the scope of this invention be determined by the appended claims and their equivalents.

What is claimed is:

1. In a multi-channel pipetting system including a plurality of passages, each of said passages for transfering a liquid volume;
    means for drawing a liquid volume into each of said passages; and
    means for expelling each of the liquid volumes from each of said passages through a pipette tip in fluid communication therewith wherein the improvement comprises
    a housing for the pipetting system;
    a plurality of pipette tip fittings with one tip fitting connected to each passage and slidably mounted on the housing enabling independent adjustment of the distance between adjacent ones of said fittings,
    and means for releasably securing each of said fittings in any desired position.

2. A pipetting system as set forth in claim 1, wherein a track is provided in said housing and said fittings are mounted on the track.

3. A multi-channel pipetting system as set forth in claim 1 wherein said means for releasably securing said fittings in any adjusted position includes a knob mounted for sliding movement on the outside of the housing;
    a clamping bar attached to said knob in the housing;
    a clamping plate attached to said clamping bar and movably mounted in the housing;
    and clamping links attached between said bar and said plate for actuating the plate to engage and secure each of the fittings when the knob is moved.

4. A multi-channel pipetting system as set forth in claim 2, wherein said means for releasably securing said fittings in any adjusted position includes a knob mounted for sliding movement on the outside of the housing;
    a clamping bar attached to said knob in the housing;
    a clamping plate attached to said clamping bar and movably mounted in the housing;
    a clamping links attached between said bar and said plate for actuating the plate to engage and secure each of the fittings when the knob is moved.

5. A pipetting system as set forth in claim 4, wherein said clamping plate engages each of said fittings and presses each against said track.

6. A pipetting system as set forth in claim 2, further comprising means for removing pipette tips attached to each of said fittings.

7. A pipetting system as set forth in claim 6, wherein said means for removing comprises:
    a trigger mounted on the housing;
    a spring attached to said trigger and biasing said trigger to a first position;
    a stripper plate movably mounted in the housing;
    and links attached between said trigger and said stripper plate for actuating the plate to engage and force the pipette tips off each of the fittings.

8. A pipetting system as set forth in claim 7, wherein said stripper plate is slotted and each of the fittings extend through the slot.

9. A pipetting system as set forth in claim 8, wherein said stripper plate has stepped edges about the slot causing the plate to engage certain ones of the tips in sequence when the trigger is actuated.

10. In a multi-channel pipetting system including a plurality of passages, each of said passages for transfering a liquid volume;
    means for drawing a liquid volume into each of said passages; and
    means for expelling each of the liquid volumes from each of said passages through a pipette tip in fluid communication therewith, wherein the improvement comprises
    a housing for the pipetting system having a plurality of fittings for holding disposable pipette tips, with one tip fitting connected to each passage,
    support means on the housing for movably supporting each of the fittings independently of one another so that the positioning of each fitting may be independently adjusted on the support means,
    an actuating means on the housing for releasably securing each of said fittings in any adjusted position.

11. A multi-channel pipetter as defined in claim 10 wherein a stripper assembly is mounted on the housing adjacent the fittings for removing pipette tips carried on each of the fittings.

12. A multi-channel pipetter as defined in claim 11 wherein the stripper assembly remains adjacent to and is arranged for removing the tips from each of the fittings regardless of the spacing between adjacent ones of the fittings.

13. A multi-channel pipetter as defined in claim 11 wherein the housing has a hand gripping portion and a lower portion carrying the means for supporting each of the fittings.

14. A multi-channel pipetter as defined in claim 13 wherein trigger means is mounted on the hand gripping portion and connected to the stripper assembly for actuating said assembly for removing the tips.

15. A multi-channel pipetter as defined in claim 13 wherein the actuating means for securing the fittings is on the lower portion of the housing and is actuable manually.

16. A multi-channel pipetter as defined in claim 10 wherein the support means for each of the fittings includes a slot in the bottom of the housing in which the fittings are slidably supported.

17. A multi-channel pipetter as defined in claim 10 wherein the fittings are aligned in a row in the support means, and one of the end fittings is held immovably in said support means.

18. In a multi-channel pipetting system including a plurality of passages, each of said passages for transferring a liquid volume;

means for drawing a liquid volume into each of said passages; and means for expelling each of the liquid volumes from each of said passages through a pipette tip in fluid communication therewith, wherein the improvement comprises a housing for the pipetting system having a handle section and a lower section, said lower section having a bottom wall, a mounting plate in the lower section adjacent the bottom wall, a plurality of tip fittings, each tip fitting connected to a passage and each removably carrying a pipette tip and movably mounted in a row on the plate, each of said fittings extending out of the bottom wall of the lower section, means enabling each fitting on the plate to move so that the spacing between adjacent ones of said fittings may be varied, and means mounted in the lower section of the housing of engaging each of the fittings and holding said fittings in a row on the plate regardless of the spacing between adjacent ones of the fittings.

19. An adjustable multi-channel pipetter as defined in claim 18 wherein a stripper is mounted on the lower section for removing the tips from each of the fittings, and a trigger is mounted on the handle section and connected to the stripper for actuating the stripper.

20. An adjustable multi-channel pipetter as defined in claim 18, wherein the means enabling each fitting to move comprises a clamping plate in the bottom wall of the housing mounted for movement between a first position in which the clamping plate secures each of the fittings to the mounting plate and a second position in which the clamping plate releases each of the fittings from the mounting plate;

and a sliding knob connected to the clamping plate for selectively moving the clamping plate between the first and second positions.

* * * * *